(12) United States Patent
Singh et al.

(10) Patent No.: US 11,578,017 B2
(45) Date of Patent: Feb. 14, 2023

(54) DIVIDING WALL COLUMN IN ALKYLATION PROCESS FOR REACTOR RECYCLE AND PRODUCT SEPARATION

(71) Applicants: Bhari Bhujan Singh, Slough (GB); Ian Charles Elgey, Slough (GB)

(72) Inventors: Bhari Bhujan Singh, Slough (GB); Ian Charles Elgey, Slough (GB)

(73) Assignee: KELLOGG BROWN & ROOT LLC, Houston, TX (US)

( * ) Notice: Subject to any disclaimer, the term of this patent is extended or adjusted under 35 U.S.C. 154(b) by 0 days.

(21) Appl. No.: 17/126,292

(22) Filed: Dec. 18, 2020

(65) Prior Publication Data
US 2021/0188737 A1 Jun. 24, 2021

Related U.S. Application Data

(60) Provisional application No. 62/950,727, filed on Dec. 19, 2019.

(51) Int. Cl.
| | |
|---|---|
| *B01D 3/14* | (2006.01) |
| *C07C 2/62* | (2006.01) |
| *B01D 3/00* | (2006.01) |
| *C07C 2/58* | (2006.01) |
| *C07C 7/04* | (2006.01) |
| *C07C 9/12* | (2006.01) |

(52) U.S. Cl.
CPC ............... *C07C 2/62* (2013.01); *B01D 3/007* (2013.01); *B01D 3/141* (2013.01); *C07C 2/58* (2013.01); *C07C 7/04* (2013.01); *C07C 9/12* (2013.01)

(58) Field of Classification Search
CPC .......... B01D 3/007; B01D 3/141; C07C 2/58; C07C 2/62; C07C 7/04; C07C 9/12
See application file for complete search history.

(56) References Cited

U.S. PATENT DOCUMENTS

| | | | |
|---|---|---|---|
| 3,068,307 A | 12/1962 | Smith | |
| 7,267,746 B1 * | 9/2007 | Harris | B01D 3/141 203/99 |
| 8,178,060 B2 * | 5/2012 | Corradi | B01D 3/14 422/600 |
| 9,683,776 B2 * | 6/2017 | Stylianou | F25J 3/0233 |
| 9,802,877 B2 * | 10/2017 | Tinger | B01D 3/141 |
| 10,150,720 B2 * | 12/2018 | Lee | B01D 3/141 |
| 10,487,022 B2 * | 11/2019 | Tinger | B01D 3/141 |
| 11,207,611 B1 * | 12/2021 | Becker | C10G 7/00 |
| 2001/0034468 A1 | 10/2001 | Mauleon et al. | |
| 2002/0197190 A1 * | 12/2002 | Schwab | C07C 5/2512 422/131 |

(Continued)

OTHER PUBLICATIONS

International Search Report and Written Opinion for International Application No. PCT/US20/65843 filed Dec. 18, 2020 received from the International Searching Authority dated Mar. 15, 2021 (14 pages).

*Primary Examiner* — Jonathan Miller (74) *Attorney, Agent, or Firm* — Gary M. Machetta (57) ABSTRACT

A dividing wall column is used in an alkylation process flow scheme to fractionate an alkylate reactor effluent to produce an iso-butane-rich stream as a recycle feed for the alkylation reactor while also separating iso-butane, normal butane and alkylate as separate product streams depending on the reactor effluent composition. In an optional embodiment, the scheme may contain propane.

17 Claims, 6 Drawing Sheets

(56) References Cited

U.S. PATENT DOCUMENTS

| | | | |
|---|---|---|---|
| 2004/0204614 A1* | 10/2004 | Groten | B01D 3/141 |
| | | | 568/38 |
| 2007/0238912 A1 | 10/2007 | Smith, Jr. et al. | |
| 2010/0303691 A1* | 12/2010 | Corradi | B01D 3/14 |
| | | | 422/608 |
| 2013/0213088 A1 | 8/2013 | Stylianou et al. | |
| 2016/0060188 A1* | 3/2016 | Tinger | C07C 2/864 |
| | | | 202/176 |
| 2016/0102032 A1 | 4/2016 | Du et al. | |
| 2017/0029348 A1* | 2/2017 | Bender | B01D 3/141 |
| 2017/0044081 A1* | 2/2017 | Kim | C07C 7/04 |

\* cited by examiner

DIVIDING WALL COLUMN IN ALKYLATION PROCESS FOR REACTOR RECYCLE AND PRODUCT SEPARATION

TECHNICAL FIELD

The present invention relates to alkylation processes for converting isoparaffins and low molecular weight alkenes into an alkylate product, and more particularly relates to such alkylation processes that include a dividing wall column.

BACKGROUND

Alkylation is a chemical process used in petroleum refining to convert isoparaffins (e.g. iso-butane) and low molecular weight alkenes (e.g. propylene, butylene, and/or amylenes) into alkylate, a high octane gasoline component. These isoparaffins and alkenes are fed into a reactor, where under the presence of a solid acid catalyst or a liquid acid catalyst (e.g. sulfuric acid or hydrofluoric acid) they combine to form alkylate. The reactor effluent is sent to a distillation train to provide product separation and to recover excess iso-butane component which is recycled back to the reactor. Amylenes are defined herein as one of a group of metameric hydrocarbons, $C_5H_{10}$, of the ethylene series.

Conventional column schemes in the distillation train include, when no propane is in the system, a conventional three-product column. In the case where propane is in the system, there is conventionally used either a four-product column potentially followed by a two-product depropanizer, or a two-product column (for separating propane from the mixture) followed by a conventional three-product column (separating iso-butane, n-butane, and an alkylate product).

It is always desirable to improve alkylation processes and systems by improving efficiency, reducing utility and energy requirements, reducing $CO_2$ and/or NOx emissions, enhancing plant safety, reducing iso-butane loss, reducing capital requirements, reducing equipment footprint requirements, and/or improving the value of the products.

SUMMARY

There is provided, in one non-limiting embodiment an alkylation system that includes an alkylation reaction/regeneration section that receives feed comprising olefin and make-up iso-butane, which alkylation reaction/regeneration section delivers alkylate reactor effluent to a dividing wall column (DWC) that also receives make-up iso-butane, where the DWC separates the alkylate reactor effluent into product streams including, but not necessarily limited to an iso-butane product stream, a n-butane product stream, and an alkylate product stream.

DETAILED DESCRIPTION

Figure 1:
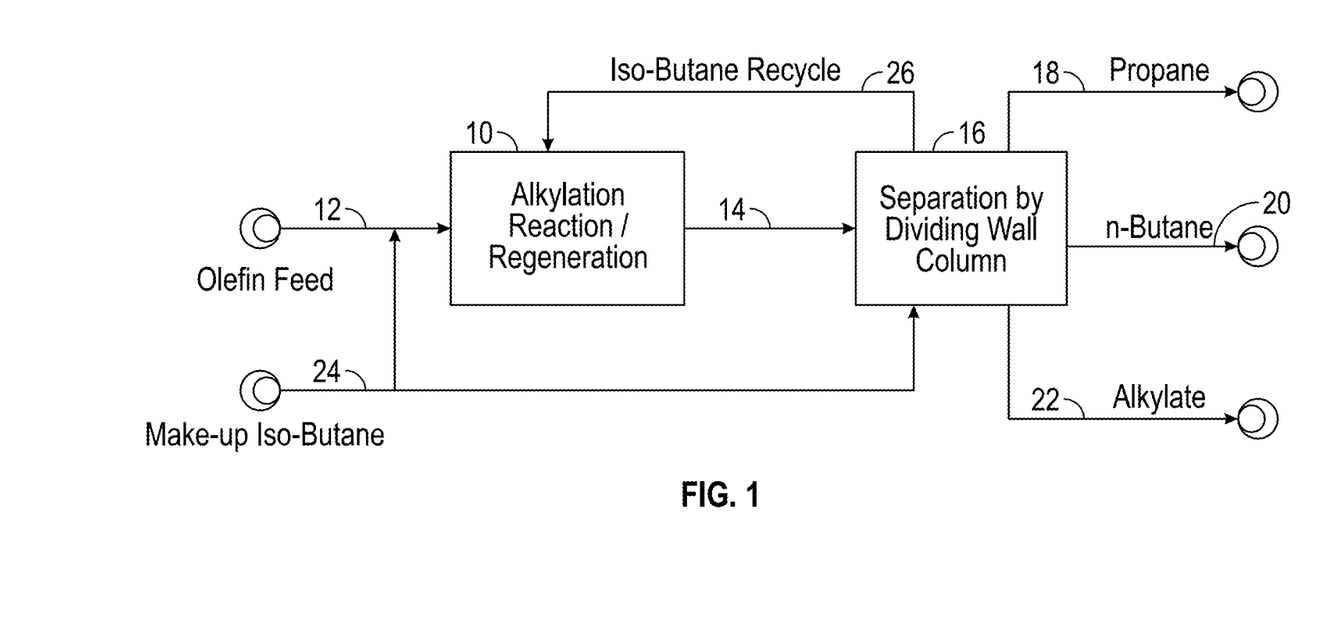
FIG. 1 is a non-limiting, schematic illustration of an alkylation plant block flow diagram illustrating separation by a dividing wall column (DWC) as described herein.

FIG. 1 shows a block flow diagram of a general alkylation process. The alkylation reaction/regeneration block configuration depends on the type of acid catalyst (solid or liquid) used in the process. The make-up iso-butane stream can be mixed with the olefin feed or fed to the fractionator depending on the composition of the make-up iso-butane stream. It has been discovered that a dividing wall column can be used as a fractionator to produce an iso-butane rich stream as a reactor recycle and simultaneously to separate various other products depending on the alkylate reactor effluent composition. Dividing wall column configurations which can be used as a fractionator block in an alkylation process are presented and discussed herein.

More specifically as shown in FIG. 1 is an alkylation reaction/regeneration section 10, sometimes simply called a reactor herein, that receives olefin feed 12 and produces alkylate reactor effluent 14 to dividing wall column 16 which separates the feed 14 into a propane-containing stream 18, a n-butane product stream 20, and an alkylate product stream 22. Also shown is make-up iso-butane 24 supplied to alkylation reactor 10 and DWC 16, as well as iso-butane recycle stream 26 from DWC 16 to reactor 10. As mentioned, the olefin feed may be propylene, butylene, and/or amylenes (C5). In one non-limiting embodiment, operators will preferentially feed the alkylation unit with butylene because this yields the highest quality alkylate (i.e. octane and vapor pressure). Also, butylene has a lower-valued alternative use than propylene. Propylene can also be used when there is an insufficient volume of butylene available and/or it is not possible to sell the propylene as a separate product. Amylenes can also be used sometimes as a supplemental feed, but this is less common.

Figure 2:
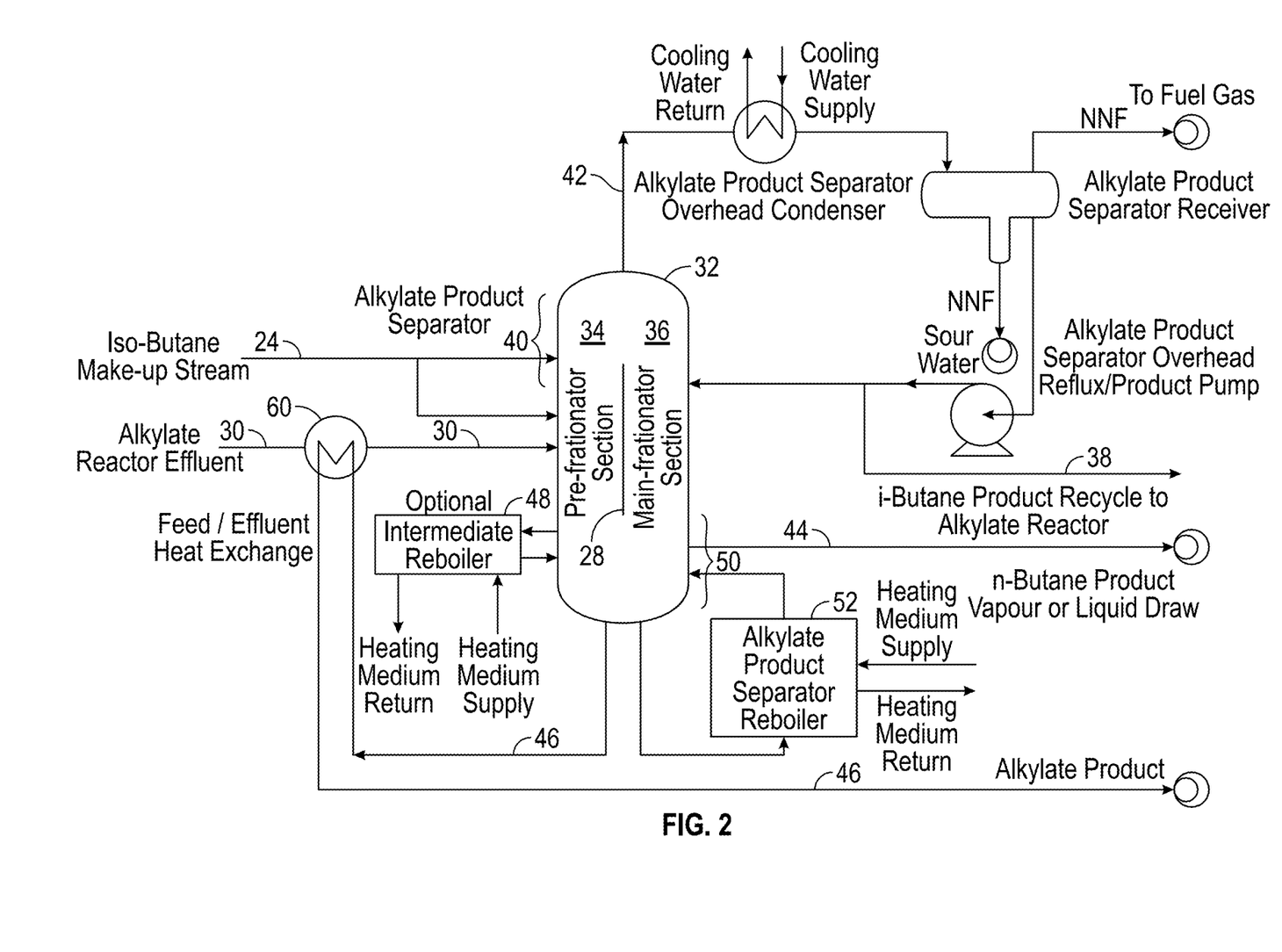
FIG. 2 is a non-limiting, schematic illustration of a flow diagram of an alkylate product separator DWC illustrating iso-butane as an overhead product and make-up stream to the DWC.
Figure 3:
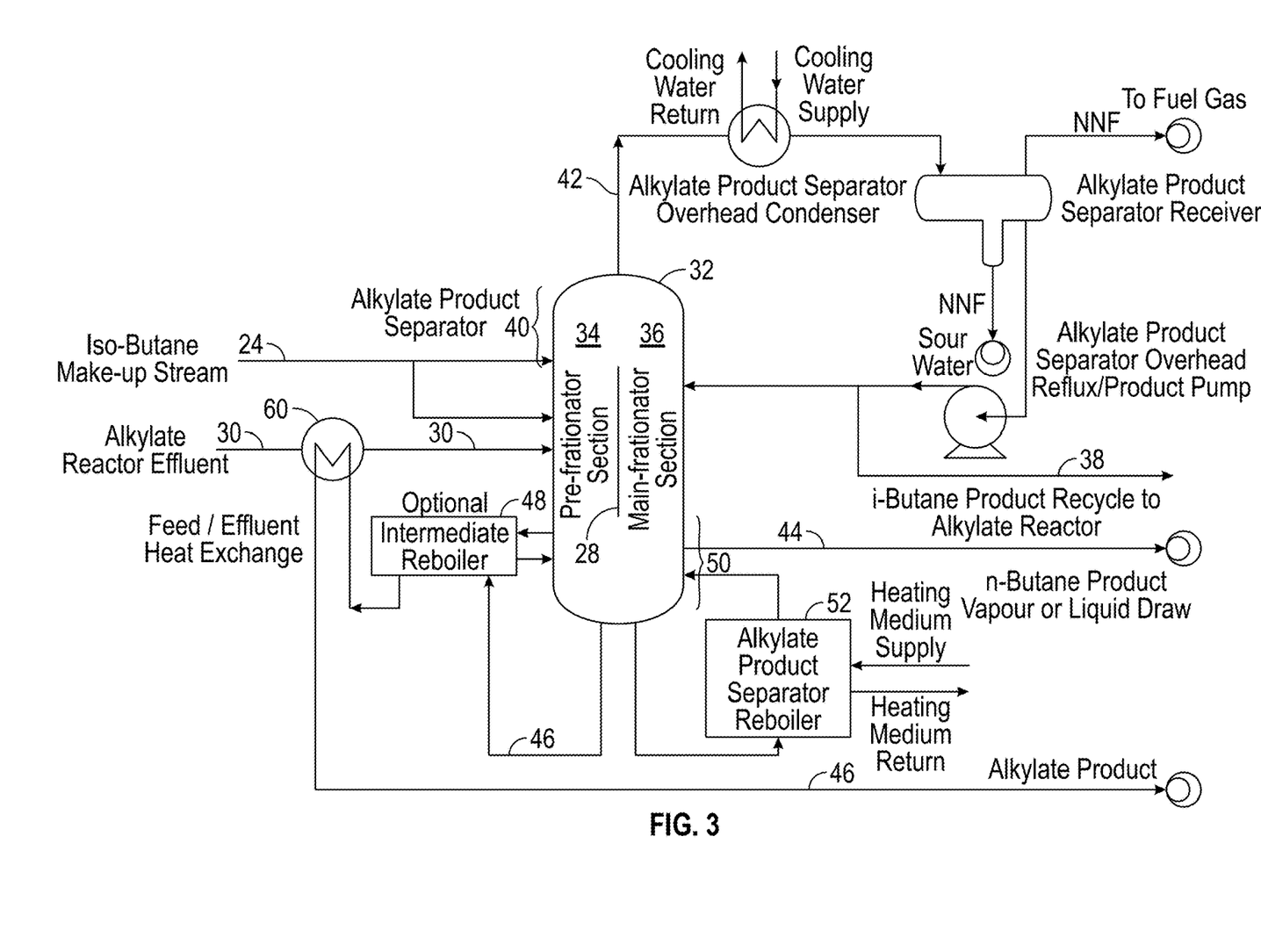
FIG. 3 is a non-limiting, schematic illustration of a flow diagram of an alkylate product separator DWC illustrating iso-butane as an overhead product and make-up stream to the DWC together with an intermediate reboiler with a bottoms product.
Figure 4:
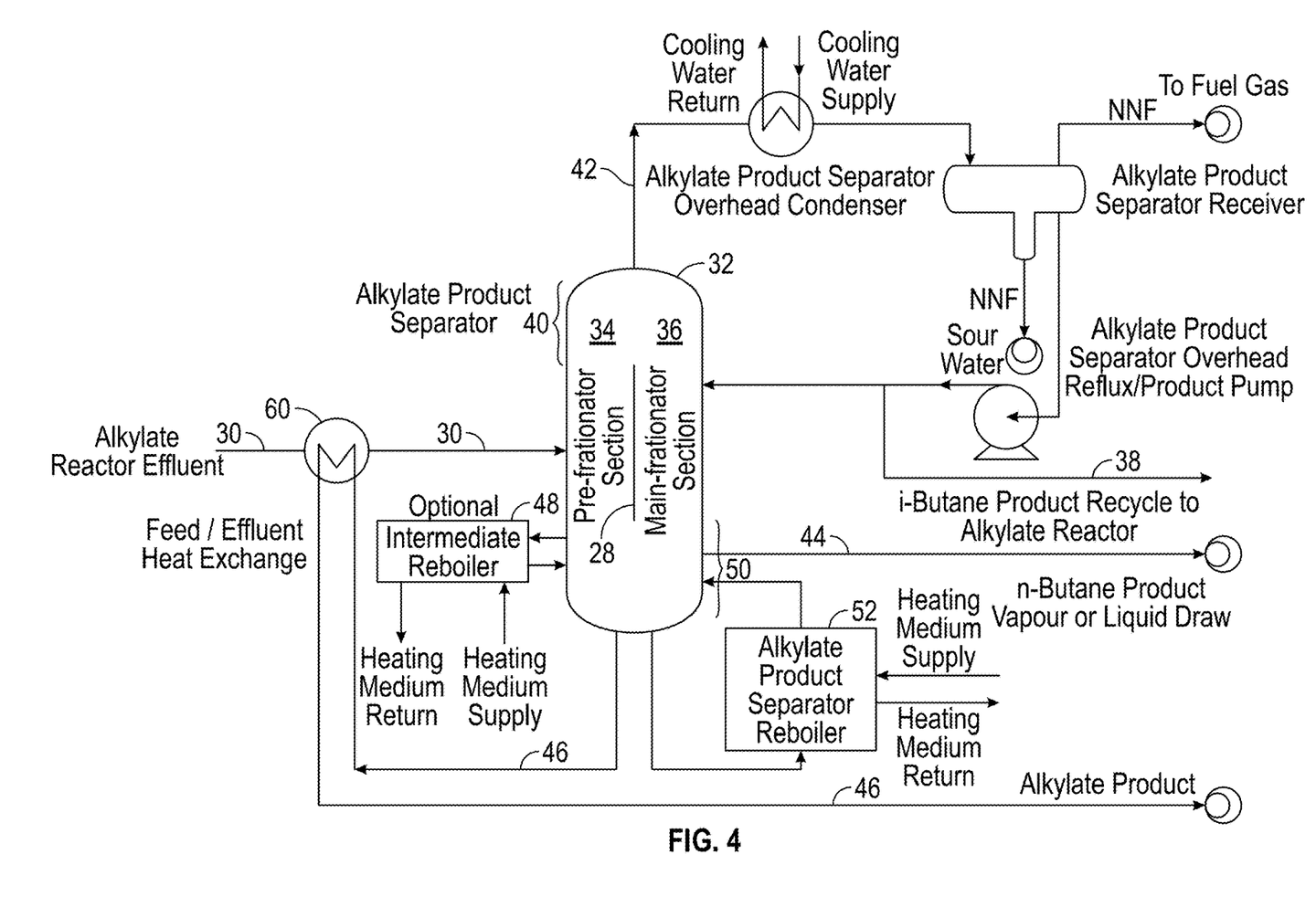
FIG. 4 is a non-limiting, schematic illustration of a flow diagram of an alkylate product separator DWC illustrating iso-butane as an overhead product.
Figure 5:
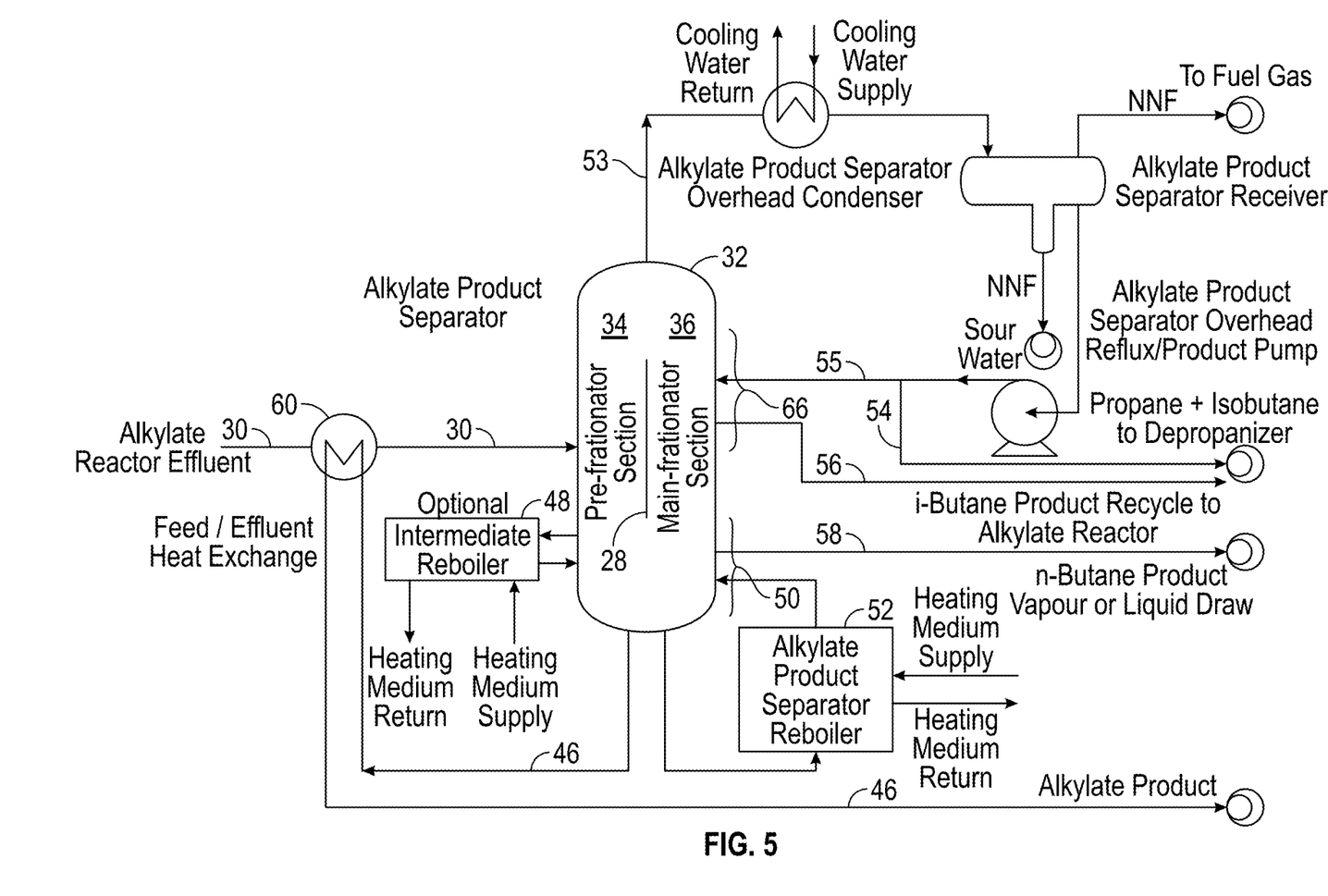
FIG. 5 is a non-limiting, schematic illustration of a flow diagram of an alkylate product separator DWC illustrating iso-butane as a side draw product.
Figure 6:
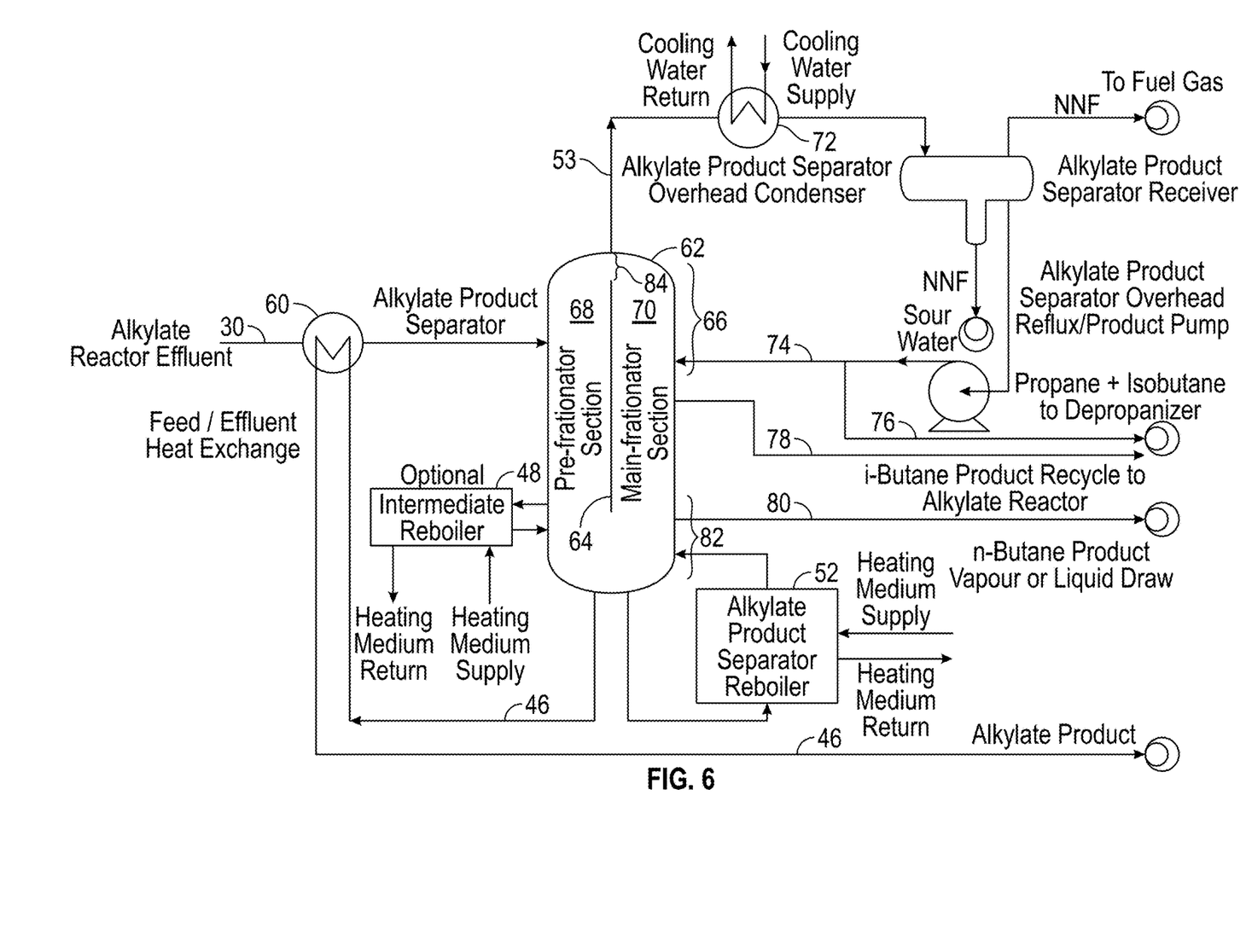
FIG. 6 is a non-limiting, schematic illustration of a flow diagram of an alkylate product separator DWC illustrating iso-butane as a side draw product together with a DWC where the dividing wall is at or near the top of the column.

While FIG. 1 schematically illustrates the general process and system herein, there are a number of more specific, non-limiting embodiments as will be discussed. In general there is a first embodiment where there is no propane present in the system as generally illustrated in FIGS. 2-4. There will also be discussed a second embodiment where there is propane present in the system as generally illustrated in FIGS. 5 and 6.

FIGS. 2 to 4 show a variety of dividing wall column configurations which can be used as an alkylation unit fractionation process, when an alkylation unit 10 does not have propane in the system and a make-up iso-butane stream 24 mainly contains C4 molecules. FIG. 2 shows a dividing wall column configuration when the alkylate reactor effluent 30 is fed to the pre-fractionator section 34 of the dividing wall column 32. DWC 32 has a main-fractionation section 36. A dividing wall 28 is present between the pre-fractionator section 34 and the main-fractionation section 36. Depending on the make-up iso-butane stream 24 composition and required iso-butane product stream 38 specification, the make-up iso-butane stream 24 can be routed to the pre-fractionator section 34 of the dividing wall and/or to the top section 40 of the dividing wall column 32. In this FIG. 2 configuration, the overhead vapor product 42 of DWC 32 will be an iso-butane rich stream which can be condensed and recycled to the alkylation reactor 10 as stream 38. The side draw product 44 will be a n-butane rich product stream, which depending on the heat integration in the plant, can be taken as a liquid or a vapor draw. Alkylate product stream 46 will be taken as a dividing wall column bottoms product. Alkylate product 46 can be routed to the battery limit after preheating the column feed 30 in heat exchanger 60. Optional intermediate reboiler(s) 48 at the lower energy level(s) can be used as an option in the bottom section 50 of the dividing wall column 32 to minimize the use of higher grade energy in the column main reboiler 52.

FIG. 3 shows a dividing wall column configuration similar to FIG. 2 except the alkylate product routing is different. FIG. 3 shows that the alkylate product 46 can be used as an intermediate reboiler 48 heating medium before it preheats the column feed 30.

FIG. 4 shows a dividing wall column configuration similar to FIG. 2 except for the make-up iso-butane stream routing. FIG. 4 assumes that the make-up iso-butane is a concentrated iso-butane stream, mixed with the olefin feed upstream of the reactor 10, and that it does not require fractionating in the fractionation section of the alkylation process. Stated another way, in one non-limiting embodiment there is an absence of a fractionation section of the alkylation reaction/regeneration section, configured to fractionating the mixture.

In another non-limiting embodiment, FIG. 5 shows a dividing wall column configuration when an alkylation unit 10 has propane in the system. The alkylate reactor effluent 30 is fed to the pre-fractionation section 34 of the dividing wall column 32. An overhead vapor stream 53 is removed from the dividing wall column 32. After condensing at least, a portion is sent to OSBL (outside battery limits) as propane rich stream 54 with possible or optional further separation in a two-product depropanizer (not shown). The balance is sent to the top section 66 of DWC 32 as alkylate product separator reflux stream 55. An iso-butane rich stream 56 can be taken from the main-fractionator section 36 of the DWC 32 as a first side draw product and recycled to the alkylate reactor 10. The first side draw product 56 can be taken as a vapor or a liquid draw as per the heat integration requirement of the system. A normal-butane rich stream 58 as a second side draw product can be taken from the main-fractionation section 36 side of the dividing wall column 32 or the bottom section 50 of the dividing wall column 32. The second side draw product 58 can be taken as a vapor or a liquid draw as per the heat integration requirement of the system. The alkylate product 46 is taken from the bottom section of the dividing wall column 32 and routed to the battery limit after heat exchange in the feed/effluent heat exchanger 60 to preheat the column feed 30. As shown in FIG. 3, the alkylate product 46 can also be used as an intermediate reboiler 48 heating medium to optimize the main reboiler energy requirement.

FIG. 6 presents a schematic illustration of another non-limiting, unique dividing wall column 62 configuration with the dividing wall panel 64 starting from the top section 66 of the column 62. The dividing wall panel 64 may start at or near the top of column 62. As defined herein, "at the top" means that there is no space between the top of the dividing wall panel 64 and the inside top of the column 62. As further defined herein, "near the top" of column 62 means a minimum of 12-inch (304.8 mm) distance 84 between the DWC 62 top tangent line and the top of the dividing wall panel 64.

The alkylate reactor effluent 30 is fed to the top tray (not shown) of the pre-fractionation section 68 of the dividing wall column 62. Vapors from the pre-fractionation section 68 and the main-fractionation section 70 are condensed in the overhead system 72 (alkylate product separator overhead condenser) and a reflux stream 74 from the overhead condenser 72 is fed to the top tray (not shown) of the main fractionation section 70 of the DWC 62. A propane rich stream 76 can be taken as a side draw from the main fractionation section 70 of the DWC 62. In one non-limiting embodiment, this propane and isobutane stream 76 is sent to a depropanizer (not shown). An iso-butane rich stream 78 can be withdrawn from the main-fractionation section 70 of the DWC 62 and sent back to the alkylate reactor 10 as a recycle stream. The second side draw product 78 can be taken as a vapor or liquid draw as per the heat integration requirement of the system. A normal-butane rich stream 80 as a third side draw product can also be taken from the main fractionator side 70 of the DWC 62 or the bottom section 82 of the dividing wall column 62. The third side draw product 80 can be taken as a vapor or liquid draw as per the heat integration requirement of the system. The alkylate product 46 is taken from the bottom section 82 of the DWC 62 and routed to the battery limit after heat exchange in the feed/effluent heat exchanger 60 to preheat the column feed 30. As shown in FIG. 3, the alkylate product can also be used as an intermediate reboiler 48 heating medium to optimize the main reboiler energy requirement.

It will be appreciated that the system and process described herein is not limited to any particular temperature ranges, pressure ranges, flow rates, stream compositions, and the like. It is expected that the system and process, now that it is described, can be modified by one of ordinary skill in the art to be applicable to a variety of reactor effluent compositions and other conditions and parameters as necessary.

It will be appreciated that the DWC can be a tray column, a packed column, or a combination of both.

It will also be appreciated that the systems and processes described herein will have a number of technical and commercial advantages. Technical advantages include, but are not necessarily limited to:
  Improvement of fractionation efficiency;
  Reduced utility requirements;
  Reduced overall energy requirements;
  Reduced $CO_2$/NOx emissions;
  Enhanced plant safety due to less hydrocarbon Inventory; and
  Reduced iso-butane loss from the system.

Commercial advantages include, but are not necessarily limited to:
  20-30% less capital requirement as compared to the conventional column solutions;
  Improvement in fractionation economics;
  Less plot space (equipment footprint) requirement;
  Advantages for plant upgrading/debottlenecking;
  Overall improvement in the value of products; and
  Alternative use of existing assets to improve the overall economics of the plant.

In the foregoing specification, the invention has been described with reference to specific embodiments thereof. However, the specification is to be regarded in an illustrative rather than a restrictive sense. For example, equipment, columns, DWCs, processes, reactants, olefins, isoparaffins, products, alkylates, and operating conditions falling within the claimed or disclosed parameters, but not specifically identified or tried in a particular example, are expected to be within the scope of this invention.

The present invention may be practiced in the absence of an ele-ment not disclosed. In addition, the present invention may suitably comprise, consist or consist essentially of the elements disclosed. For instance, there may be provided an alkylation system, where the alkylation system consists essentially of or consists of an alkylation reaction/regeneration section that receives feed comprising olefin and make-up iso-butane, which alkylation reaction/regeneration section delivers alkylate reactor effluent to a dividing wall column (DWC) that also receives make-up iso-butane, where the DWC separates the alkylate reactor effluent into product streams comprising, consisting essentially of, or consisting of an iso-butane product stream, a n-butane product stream, and an alkylate product stream.

The words "comprising" and "comprises" as used throughout the claims, are to be interpreted to mean "including but not limited to" and "includes but not limited to", respectively.

As used herein, the word "substantially" shall mean "being largely but not wholly that which is specified."

As used herein, the singular forms "a," "an," and "the" are intended to include the plural forms as well, unless the context clearly indicates otherwise.

As used herein, the term "about" in reference to a given parameter is inclusive of the stated value and has the meaning dictated by the context (e.g., it includes the degree of error associated with measurement of the given parameter).

As used herein, the term "and/or" includes any and all combina-tions of one or more of the associated listed items.
    the DWC (16) has a side draw product that is a n-butane-rich stream (44) that is the n-butane product stream (20); and
    the DWC (16) has a bottoms product (46) that is the alkylate product stream (22).

What is claimed is:

1. An alkylation system comprising:
an alkylation reaction/regeneration section (10) that receives a feed comprising olefin (12) and make-up iso-butane (24), which alkylation reaction/regeneration section (10) produces an alkylate reactor effluent (14);
a dividing wall column (DWC) (16) that receives the alkylate reactor effluent and that also receives make-up iso-butane (24), where the DWC (16) separates the alkylate reactor effluent (14) into streams comprising:
an iso-butane recycle stream (38),
a n-butane product stream (20), and
an alkylate product stream (22);
where at least a portion of the iso-butane recycle stream (38) is recycled to the alkylation reaction/regeneration section (10) in a recycle stream (26).

2. The alkylation system of claim 1 where the DVC (16) also separates the alkylate reactor effluent (14) into a propane stream (18) along with the iso-butane recycle stream (38), n-butane product stream (20), and alkylate product stream (22).

3. The alkylation system of claim 1 or 2 where:
the alkylate reactor effluent (14) is a feed to a pre-fractionator section (34) of the DWC (16);
make-up iso-butane (24) is a feed to the pre-fractionator section (34) of the DWC (16);
the DWC (16) has an overhead iso-butane-rich stream (42) that is the iso-butane recycle stream (38);
the DWC (16) has a side draw product that is a n-butane-rich stream (44) that is the n-butane product stream (20); and
the DWC (16) has a bottoms product (46) that is the alkylate product stream (22).

4. The alkylation system of claim 3 where the alkylate product stream (22) is routed to a battery limit after pre-heating the alkylate reactor effluent (14) in a heat exchanger (60) prior to being fed to the DWC (16).

5. The alkylation system of claim 3 further comprising an intermediate reboiler (48) in a bottom section (50) of the DWC (16).

6. The alkylation system of claim 5 where the alkylate product stream (22) is a heating medium in the intermediate reboiler (48) before the alkylate product stream (22) pre-heats the alkylate reactor effluent (30).

7. The alkylation system of claim 3 where at least a portion of the make-up iso-butane (24) comprises at least a portion of the iso-butane recycle stream (38) and the make-up iso-butane (24) is routed to the olefin feed (12) upstream of the alkylation reaction/regeneration section (10) to form a mixture.

8. The alkylation system of claim 7 where the mixture is directly delivered to the alkylation reaction/regeneration section (10) without a fractionation section, configured for fractionating the mixture.

9. The alkylation system of claim 1 or 2 where:
the alkylate reactor effluent (14) containing propane is a feed to a pre-fractionator section (34) of the DWC (16);
the DWC (16) has an overhead product containing propane (54) routed to a depropanizer column;
the DWC (16) has an iso-butane-rich stream that is the iso-butane recycle stream (38) as a first side draw product (56), taken from a main-fractionator section (36) of the DWC (16), where the iso-butane recycle stream (38) is recycled to the alkylation reaction/regeneration section;
the DWC (16) has a n-butane-rich stream (58) that is the n-butane product stream (20) as a second side draw product (58), taken from the main-fractionator section (36) of the DWC (16) or a bottoms section (50) of the DWC (16), where the second side draw product (58) is selected from the group consisting of vapor, liquid, or a combination thereof; and
the DWC (16) has a bottoms product (46) that is the alkylate product stream (22).

10. The alkylation system of claim 9 where the alkylate product stream (46) is routed to a battery limit after pre-heating the alkylate reactor effluent (30) in a heat exchanger (60) prior to being fed to the DWC (16).

11. The alkylation system of claim 9 further comprising an intermediate reboiler (48) in a bottom section (50) of the DWC (16), and where the alkylate product stream (22) is a heating medium in the intermediate reboiler (48).

12. The alkylation system of claim 9 where the DWC (16) comprises a dividing wall panel (28) starting at or near the top of the column (32) and extending downward.

13. The alkylation system of claim 12 where:
the alkylate reactor effluent (30) is fed to a top tray of the pre-fractionator section (34) of the DWC (16);
the DWC (16) comprises an overhead condenser (72) configured to condense vapors from the pre-fractionator section (34) and the main fractionator section (36); and a reflux stream (74) from the overhead condenser (72) is fed to a top tray of the main fractionator section (36).

14. The alkylation system of claim 12 where a propane-rich stream is taken as a side draw (76) from the main fractionator section (36).

15. The alkylation system of claim 12 where a third side draw is a n-butane-rich stream (80) taken from a point selected from the group consisting of the main fractionator section (36) and a bottom section (82) of the DWC (16).

16. The alkylation system of claim 12 where the alkylate product stream (22) is routed to a battery limit after pre-heating the alkylate reactor effluent (14) in a heat exchanger prior to being fed to the DWC (16).

17. The alkylation system of claim 12 further comprising an intermediate reboiler (48) in a bottom section of the DWC (16), and where the alkylate product stream (22) is a heating medium in the intermediate reboiler (48).

\* \* \* \* \*